United States Patent
Wang et al.

(10) Patent No.: US 11,377,397 B2
(45) Date of Patent: Jul. 5, 2022

(54) PRODUCTION OF CYCLOPENTADIENE FROM FURFURAL

(71) Applicant: ExxonMobil Technology and Engineering Company, Annandale, NJ (US)

(72) Inventors: Kun Wang, Branchburg, NJ (US); Aaron Sattler, Annandale, NJ (US); Jihad M. Dakka, Whitehouse Station, NJ (US)

(73) Assignee: ExxonMobil Technology and Engineering Company, Annandale, NJ (US)

( * ) Notice: Subject to any disclaimer, the term of this patent is extended or adjusted under 35 U.S.C. 154(b) by 127 days.

(21) Appl. No.: 17/077,327

(22) Filed: Oct. 22, 2020

(65) Prior Publication Data
US 2021/0188735 A1    Jun. 24, 2021

Related U.S. Application Data

(60) Provisional application No. 62/951,048, filed on Dec. 20, 2019.

(51) Int. Cl.
| | |
|---|---|
| *C07C 1/24* | (2006.01) |
| *C07C 13/12* | (2006.01) |
| *C07C 13/15* | (2006.01) |
| *C07C 1/247* | (2006.01) |
| *B01J 8/00* | (2006.01) |

(52) U.S. Cl.
CPC ............... *C07C 1/24* (2013.01); *B01J 8/008* (2013.01); *C07C 1/247* (2013.01); *B01J 2208/06* (2013.01); *C07C 13/12* (2013.01); *C07C 13/15* (2013.01); *C07C 2529/068* (2013.01)

(58) Field of Classification Search
CPC .......... C07C 1/24; C07C 1/247; C07C 13/12; C07C 13/15; C07C 2529/068; B01J 8/008; B01J 2208/06
See application file for complete search history.

(56) References Cited

U.S. PATENT DOCUMENTS 11,078,139 B1 *   8/2021   Harvey ............... C07C 1/24

OTHER PUBLICATIONS

Mironenko et al. (Palladium-Ruthenium Catalyst for Selective Hydrogenation of Furfural to Cyclopentanol. Kinet Catal 59, 339-346 (2018)) (Year: 2018).*
Li et al. (Selective conversion of furfural to cyclopentanone or cyclopentanol using different preparation methods of Cu—Co catalysts. Green Chem. 2015, 17, 1038) (Year: 2015).*
Chen et al. (Synthesis of High-Density Aviation Fuel with Cyclopentanol. ACS Sustainable Chem. Eng. 2016, 4, 6160-6166) (Year: 2016).*
Minghao Zhou, "Aqueous-phase catalytic hydrogenation of furfural to cyclopentanol over Cu—Mg—Al hydrotalcites derived catalysts: Model reaction for upgrading of bio-oil", Journal of Energy Chemistry, Jan. 2014, pp. 91-96, vol. 23, Issue 1, Science Direct.
Minghao Zhou, "Catalytic Hydroprocessing of Furfural to Cyclopentanol Over Ni/CNTs Catalysts: Model Reaction for Upgrading of Bio-oil", Catal Lett, 2014, pp. 235-241, vol. 144, New York.
Natalia Pino, "Selective Catalytic Route for the Synthesis of High-Density Biofuel Using Biomass-Derived Compounds", Energy Fuels, 2018, pp. 561-573, vol. 32, Colombia.
Yuan Wang, "CuNi@C catalysts with high activity derived from metal-organic frameworks precursor for conversion of furfural to cyclopentanone", Chemical Engineering Journal, 2016, pp. 104-111, vol. 299, China.
Yanhua Liu, "Highly Selective and Efficient Rearrangement of Biomass-Derived Furfural to Cyclopentanone over Interface-Active Ru/Carbon Nanotubes Catalyst in Water", ACS Sustainable Chemistry & Engineering, 2017, pp. 744-751, vol. 5, China.
Milan Hronec, "Selective transformation of furfural to cyclopentanone", Catalysis Communication, 2012, pp. 100-104, vol. 24, Slovakia.
Milan Hronec, "Influence of furanic polymers on selectivity of furfural rearrangement to cyclopentanone", Applied Catalysis A: General, 2013, pp. 426-431, vol. 468, Slovakia.
Milan Hronec, "Highly selective rearrangement of furfuryl alcohol to cyclopentanone", Applied Catalysis B: Environmental, 2014, pp. 294-300, vol. 154, Slovakia.
Milan Hronec, "Carbon supported Pd—Cu catalysts for highly selective rearrangement of furfural to cyclopentanone", Applied Catalysis B: Environmental, 2016, pp. 210-219, vol. 181, Slovakia.
Guangyi Li, "Synthesis of Diesel or Jet Fuel Range Cycloalkanes with 2-methylfuran and Cyclopentanone from Lignocellulose", Energy & Fuels, 2014, pp. 5112-5118, vol. 28, China.
Claudia Piutti, "The Piancatelli Rearrangement: New Applications for an Intriguing Reaction", Molecules, 2013, pp. 12290-12312, vol. 18.
Surapas Sitthisa, "Hydrodeoxygenation of Furfural Over Supported Metal Catalysys: A Comparative Study of Cu, Pd and Ni" Catal Lett, 2011, pp. 784-791, vol. 141.
Milan Hronec, "Effect of catalyst and solvent on the furan ring rearrangement to cyclopentanone", Applied Catalysis A: General, 2012, pp. 104-111, vol. 437, Slovakia.
Natalia Pino, "Hydrophobic zeolites for the upgrading of biomass-derived short oxygenated compounds in water/oil emulsions" Applied Catalysis A, General, 2018, pp. 94-101, Norman, OK.
Charles M. Cai, "Integrated furfural production as a renewable fuel and chemical platform from lignocellulosic biomass", J Chem Technol Biotechnol, 2014, pp. 2-10, vol. 89.

(Continued)

*Primary Examiner* — In Suk C Bullock
*Assistant Examiner* — Jason Y Chong
(74) *Attorney, Agent, or Firm* — Robert A. Migliorini

(57) ABSTRACT

The application relates to processes and systems that use a furfural compound for producing five-membered carbocyclic rings that are unsaturated, such as cyclopentene and cyclopentadiene. Examples methods for conversion of furfural compounds may include converting a furfural compound to at least a five-membered, saturated carbocyclic ring, and converting the five-membered, saturated carbocyclic ring in a presence of a catalyst to at least a five-membered, unsaturated carbocyclic ring.

16 Claims, No Drawings

(56) References Cited

OTHER PUBLICATIONS

B.M. Nagaraja, "A highly acrive Cu—MgO—Cr2O3 catalyst for simultaneous synthesis of furfuryl alcohol and cyclohexanone by a novel coupling route—Combination of furfural hydrogenation and cyclohexanol dehydrogenation", Science Direct, 2007, pp. 29-37, vol. 278, India.

C. A. Grob, "Eine neue Pyrrolring-Synthese", Helvetica Chimica Acta., 1953, vol. 36, p. 268-274.

* cited by examiner

PRODUCTION OF CYCLOPENTADIENE FROM FURFURAL

FIELD

This application relates to processes and systems that use a furfural compound for producing five-membered carbocyclic rings that are unsaturated, such as cyclopentene and cyclopentadiene.

BACKGROUND

Cyclopentadiene is a five-membered carbocyclic ring. Cyclopentadiene can be a valuable intermediate in the production of a number of different end products. For instance, cyclopentadiene may be used as a monomer to synthesize polycyclopentadiene and C5 hydrocarbon resins and adhesives. Cyclopentadiene can dimerize to make dicyclopentadiene, which may be used as a monomer to synthesize polydicyclopentadiene rubbers. Cyclopentene may also be used as a monomer to make polymers, resins, and adhesives. Cyclopentadienes and substituted cyclopentadienes may be used as a precursor for formation of cyclopentadienyl ligands, which can be useful in the preparation of catalysts. Current production of cyclopentadiene typically comes from products in naphtha steam crackers and fluid catalytic crackers.

SUMMARY

Disclosed herein is an example method for conversion of furfural compounds. The method may comprise converting a furfural compound to at least a five-membered, saturated carbocyclic ring. The method may further comprise converting the five-membered, saturated carbocyclic ring in a presence of a catalyst to at least a five-membered, unsaturated carbocyclic ring, wherein the five-membered, unsaturated carbocyclic ring is selected from the group consisting of a cyclopentene product, a cyclopentadiene product, and combinations thereof.

Further disclosed herein is an example method for conversion of furfural compounds. The method may comprise contacting furfural and hydrogen with a catalyst to produce at least a five-membered, saturated carbocyclic ring, wherein the five-membered, saturated carbocyclic ring is selected from the group consisting of cyclopentanol, cyclopentanone, cyclopentanediol, and combinations thereof. The method may comprise contacting the five-membered, saturated carbocyclic ring with a catalyst to produce at least water and a five-membered, unsaturated carbocyclic ring, wherein the five-membered, unsaturated carbocyclic ring is selected from the group consisting of cyclopentene, cyclopentadiene, and combinations thereof.

Further disclosed herein is an example method for conversion of furfural compounds. The method may comprise hydrogenating furfural by catalytically reacting the furfural and hydrogen to produce a five-membered, saturated carbocyclic ring, wherein the five-membered, saturated carbocyclic ring is selected from the group consisting of cyclopentanol, cyclopentanone, cyclopentanediol and combinations thereof. The method may further comprise converting the five-membered, saturated carbocyclic ring to cyclopentadiene.

DETAILED DESCRIPTION

This application relates to processes and systems that use a furfural compound for producing five-membered carbocyclic rings that are unsaturated, such as cyclopentene and cyclopentadiene. As used herein, the term "furfural compound" refers to furfural and substituted furfurals.

There may be several potential advantages to the methods and systems disclosed herein, only some of which may be alluded to in the present disclosure. Advantageously, embodiments disclosed herein can provide favorable reaction thermodynamics than starting with other feeds such as n-pentane, as the embodiments may only include (a) dehydration or (b) dehydration and dehydrogenation with one equivalent of $H_2$. Additionally, embodiments may use furfural compounds as the feed for the production of the cyclopentadiene or other five-membered, unsaturated carbocyclic rings. As the energy intensity of the conversion of the furfural compound may be low, production of the desired five-membered, unsaturated carbocyclic rings may be favored. Moreover, since furfural compounds may be bio-derived (e.g., from xylose, arabinose, etc.), the furfural compounds may be considered a renewable feedstock for the synthesis of cyclopentadiene or other five-membered, unsaturated carbocyclic rings, which can then be converted to valuable products.

Embodiments may include conversion of a furfural compound to a five-membered, unsaturated carbocyclic ring. In at least one embodiment, furfural may be converted to either cyclopentadiene and/or cyclopentene. The process may first include conversion of the furfural compound to a five-membered carbocyclic ring, such as a cyclopentanol compound, a cyclopentanone compound, and/or cyclopentanediol compound. The five-membered carbocyclic ring can then be dehydrated and, if needed, dehydrogenated, to form the five-membered, unsaturated carbocyclic ring, such as a cyclopentene product and/or a cyclopentadiene product. In some embodiments, the cyclopentene product may be dehydrogenated to produce a cyclopentadiene product. In some embodiments, the conversion may be performed in a single step, for example using a bi-functional catalyst that can both hydrogenate/dehydrogenate and dehydrate, to form the five-membered, unsaturated carbocyclic ring from the furfural compound.

The furfural compounds may include furfural, substituted furfurals, or combinations thereof. Furfural is an organic compound than can be bioderived. For example, furfural can be derived from the dehydration of 5-carbon sugars, such as xylose or arabinose. Substituted furfurals may also be derived from 5-carbon sugars. Examples of suitable furfural compounds may be represented by the following structure:

Structure 1

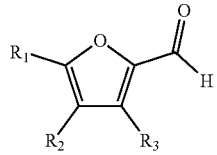

Where R1, R2, and R3 may be individually selected from hydrogen or a hydrocarbyl group containing 1 carbon atom to 10 atoms, wherein the hydrocarbyl group may be linear, branched, or cyclic, and wherein the cyclic hydrocarbyl may aromatic or non-aromatic. The hydrocarbyl group may be substituted or unsubstituted. Alternatively, two or more of R1, R2, and R3 may be connected as part of a ring with 4 carbon atoms to 14 carbons atoms, for example. The ring may to be saturated or have multiple degrees of unsaturation, for example, without being aromatic.

The furfural compound may be converted to the five-membered, saturated carbocyclic ring, for example, by the catalyzed reaction of the furfural compound in the presence or absence of hydrogen. The reaction may be conducted in the liquid phase or gas phase, with or without a co-feed such as water. The reaction may be carried out, for example, with any suitable catalyst. Suitable catalysts may include, but are not limited to, metal oxides such as chromium oxide, zinc oxide, vanadium oxide, gallium oxide, rhenium oxide, osmium oxide, ruthenium oxide, iridium oxide, hydrotalcites, metals such as Ni, Co, Fe, Cu, Zn, Pt, Pd, Rh, Ru, Ir, Au, supported metals, clays, aluminosilicates, layered double hydroxides, and amorphous materials. In some embodiments, the catalyst may be a supported catalyst that includes a catalyst deposited on a support. Examples of suitable supports may include, but are not limited to, refractory oxides such as titania and/or zirconia; silica; activated carbon; carbon on which is deposited one or more metals selected from titanium, zirconium, vanadium, molybdenum, manganese, and cerium; magnesium oxides; hydrotalcites; other various types of clays; metal-organic frameworks (MOF) and combinations thereof, such as a mixture of two or more of titania, zirconia, and silica. Exemplary catalysts are Pt/C, Pd—Cu/C, and Ni based catalysts such as Ni—Cu or Cu—Co supported on refractory oxides shown above or zeolites (e.g., Faujasite) or mesoporous materials (e.g., MCM-41, SBA-15), Ru supported on refractory oxides shown above or zeolites (e.g., Faujasite) or mesoporous materials (e.g., MCM-41, SBA-15), CuZnAl oxides, and CuNiAl. In some embodiments, suitable catalysts may include bifunctional catalysts that contain hydrogenation dehydrogenation metal functionality and a heterogenous acid component. Examples of suitable hydrogenation dehydrogenation metal functionality may include, but are not limited to, Sn, Pd, Pt, Ni, Rh, Ru, Ni, Co, and combinations thereof. Examples of suitable acid components may include a heterogeneous acid component, for example, zeolite, mixed metal oxides, and resins, which may have an alpha test value of less than 100 and, in some embodiments, less than 50. An alpha test can be used to determine acidity of a material, which is the n-hexane decomposition activity on a material. In the alpha test, n-hexane is sparged into a stream of helium which is ultimately passed through the reactors containing the test component at elevated temperatures (1000° F.). During the run, an in-line GC is used to analyze the reactor effluent to determine hexane conversion. The hexane conversion of the acidic material is referenced to that of silica, which is defined to have an alpha value of 1. In some embodiments, the loading of metal on the acidic component may be in the range of about 0.1 wt % to about 5 wt % (referenced to the catalyst weight), or about 0.3 wt % to about 3 wt %, or about 0.5 wt % to about 2 wt %. When the acidic component is an inorganic acid, in some embodiments, the acidic component can be self-bonded or bonded using a binder such as silica, alumina, titania, zirconia, clay (e.g., Kaolin), or combinations thereof. Examples of the acidic component include zeolites having the structure of MFI, MWW, BEA, MOR, or FAU. Optionally, the zeolite component can be further stabilized using phosphorus, rare earths such as lanthanum, yttrium. When the acidic component is mixed metal oxides, in some embodiments, examples of mixed metal oxides may include zirconium tungsten oxides, zirconium molybdenum oxides, sulfated zirconia, or mixtures thereof. A specific example of bifunctional catalyst may include a metal functionality of Sn—Pt and an acid component of a zeolite, for example, Pt—Sn/ZSM-5 or Pt—Sn/MCM-49. Another example of a specific catalyst may include a metal functionality of Pt and an acid component of a zeolite such as Pt/MCM-49.

Any suitable ratio of the furfural compound to the catalyst may be suitable for conversion to the five-membered, unsaturated carbocyclic ring. For example, the weight ratio of the furfural compound to the catalyst may be about 5:1 to about 1000000:1. In some embodiments, the weight ratio of the furfural compound to the catalyst may be about 50:1 to about 1000:1.

The conversion of the furfural compound to the five-membered, saturated carbocyclic ring may be conducted at conditions sufficient to form the desired five-membered, saturated carbocyclic ring. For example, the furfural conversion may occur at a temperature of about 20° C. to about 400° C., and optionally at a temperature of about 20° C. to about 300° C. In some embodiments, the furfural conversion may be at a pressure of about 15 psig (103 kPa) to about 1000 psig (6890 kPa).

When the furfural compound and the hydrogen are contacted by the catalyst, the furfural compound may be converted to the five-membered, saturated carbocyclic ring. In some embodiments, the five-membered, unsaturated carbocyclic ring may include cyclopentanol compounds, cyclopentanone compounds, cyclopentanediol compounds, and combinations thereof.

The cyclopentanol compounds may include cyclopentanol, substituted cyclopentanol, or combinations thereof. Examples of suitable cyclopentanol compounds may be represented by the following structure:

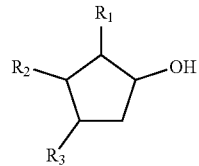

Structure 2

Where $R_1$, $R_2$, and $R_3$ may be individually selected from hydrogen or a hydrocarbyl group containing 1 carbon atom to 10 atoms, wherein the hydrocarbyl group may be linear, branched, or cyclic, and wherein the cyclic hydrocarbyl may aromatic or non-aromatic. The hydrocarbyl group may be substituted or unsubstituted. Alternatively, two or more of $R_1$, $R_2$, and $R_3$ may be connected as part of a ring with 4 carbon atoms to 14 carbons atoms, for example. The ring may be saturated or have multiple degrees of unsaturation, for example, without being aromatic.

The cyclopentanone compounds may include cyclopentanone, substituted cyclopentanone, or combinations thereof. Examples of suitable cyclopentanone compounds may be represented by the following structure:

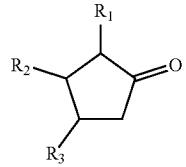

Structure 3

Where R1, R2, and R3 may be individually selected from hydrogen or a hydrocarbyl group containing 1 carbon atom to 10 atoms, wherein the hydrocarbyl group may be linear, branched, or cyclic, and wherein the cyclic hydrocarbyl may aromatic or non-aromatic. The hydrocarbyl group may be substituted or unsubstituted. Alternatively, two or more of R1, R2, and R3 may be connected as part of a ring with 4 carbon atoms to 14 carbons atoms, for example. The ring may be saturated or have multiple degrees of unsaturation, for example, without being aromatic.

The cyclopentanediol compounds may include cyclopentanediol, substituted cyclopentanediol, or combinations thereof. Special cyclopentanediols that may be suitable include, but are not limited to cyclopetane-1,3-diol. Examples of suitable cyyclopentane-1,3-diol compounds may be represented by the following structure:

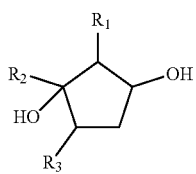

Structure 4

Where R1, R2, and R3 may be individually selected from hydrogen or a hydrocarbyl group containing 1 carbon atom to 10 atoms, wherein the hydrocarbyl group may be linear, branched, or cyclic, and wherein the cyclic hydrocarbyl may aromatic or non-aromatic. The hydrocarbyl group may be substituted or unsubstituted. Alternatively, two or more of R1, R2, and R3 may be connected as part of a ring with 4 carbon atoms to 14 carbons atoms, for example. The ring may be saturated or have multiple degrees of unsaturation, for example, without being aromatic.

Embodiments may include conversion of the five-membered, saturated carbocyclic ring to the desired five-membered, unsaturated carbocyclic ring, such as a cyclopentene product and/or a cyclopentadiene product. For example, the five-membered, saturated carbocyclic ring may be dehydrated to produce the five-membered, unsaturated carbocyclic ring. Advantageously, embodiments may not require purification from other refinery streams with different carbon numbers of the reaction products (e.g., the five-membered, unsaturated carbocyclic ring) from the furfural conversion prior to dehydration. In some embodiments, a cyclopentanol product may be dehydrated to form cyclopentene. In some embodiments, a cyclopentanol product may be dehydrated and dehydrogenated to form cyclopentadiene. In some embodiments, a cyclopentanone product may be dehydrated to form cyclopentadiene. In some embodiments, a cyclopentanediol product (e.g., cyclopentane-1,3-diol) may be dehydrated to form cyclopentadiene.

In at least one embodiment, conversion to the five-membered, unsaturated carbocyclic ring may include dehydration of a cyclopentanol compound to a cyclopentene product. The dehydration reaction may be conducted in the liquid phase or gas phase. In some embodiments, an acid catalyst may be used, for example, to catalyze the dehydration. The cyclopentanol dehydration can generally take place at conditions sufficient to form water and the cyclopentene product. For example, the cyclopentanol conversion may occur at a temperature of about 25° C. to about 300° C.

In some embodiments, the cyclopentanol conversion may be at a pressure of about 15 psig (103 kPa) to about 1000 psig (6890 kPa).

When the cyclopentanol compound is contacted by the catalyst, the cyclopentanol compound may be converted to a cyclopentene product. In some embodiments, the cyclopentene product may include cyclopentene, substituted cyclopentene, and combinations thereof. Examples of suitable cyclopentene products may be represented by either of the following structures:

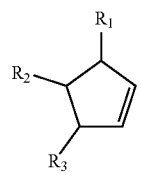

Structure 5

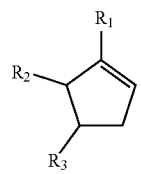

Structure 6

Where R1, R2, and R3 may be individually selected from hydrogen or a hydrocarbyl group containing 1 carbon atom to 10 atoms, wherein the hydrocarbyl group may be linear, branched, or cyclic, and wherein the cyclic hydrocarbyl may aromatic or non-aromatic. The hydrocarbyl group may be substituted or unsubstituted. Alternatively, two or more of R1, R2, and R3 may be connected as part of a ring with 4 carbon atoms to 14 carbons atoms, for example. The ring may be saturated or have multiple degrees of unsaturation, for example, without being aromatic.

In at least one embodiment, conversion to the five-membered, unsaturated carbocyclic ring may include conversion of the cyclopentene product to a cyclopentadiene product. For example, the product compound may be dehydrogenated to produce hydrogen and the cyclopentadiene product. The dehydrogenation reaction may be conducted in the liquid phase or gas phase. Suitable dehydrogenation catalyst may include, for example, at least one metal. Examples of suitable metals may include, but are not limited to, copper, cobalt, iron, nickel, gallium, zinc, ruthenium, rhodium, palladium, silver, osmium, iridium, platinum, gold, and combinations thereof. Catalysts can also include other metals, such as chromium or vanadium. In some embodiments, the catalysts can also contain two metals, such as platinum and tin, platinum and silver, platinum and zinc, platinum and gallium, platinum and rhenium, platinum and gold, platinum and copper, palladium and copper, copper and nickel, copper and cobalt.

The cyclopentene dehydrogenation can generally take place at conditions sufficient to form hydrogen and the cyclopentadiene product. For example, the cyclopentene dehydrogenation may occur at a temperature of about 300° C. to about 650° C. In some embodiments, the cyclopentene dehydrogenation may be at a pressure of about vacuum to about 100 psig (690 kPa).

When the cyclopentene product is contacted by the catalyst, the cyclopentene product may be converted to a cyclopentadiene product. In some embodiments, the cyclopentadiene product may include cyclopentadiene, substituted cyclopentadiene, and combinations thereof. Examples of suitable cyclopentadiene compounds may be represented by either of the following structures:

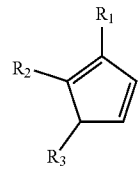

Structure 7

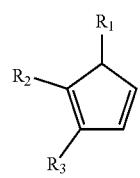

Structure 8

Where R1, R2, and R3 may be individually selected from hydrogen or a hydrocarbyl group containing 1 carbon atom to 10 atoms, wherein the hydrocarbyl group may be linear, branched, or cyclic, and wherein the cyclic hydrocarbyl may aromatic or non-aromatic. The hydrocarbyl group may be substituted or unsubstituted. Alternatively, two or more of R1, R2, and R3 may be connected as part of a ring with 4 carbon atoms to 14 carbons atoms, for example. The ring may be saturated or have multiple degrees of unsaturation, for example, without being aromatic.

In at least one embodiment, conversion to the five-membered, unsaturated carbocyclic ring may include dehydration of a cyclopentanone compound to a cyclopentadiene product. The dehydration reaction may be conducted in the liquid phase or gas phase. The dehydration reaction may be carried out, for example, with any suitable catalyst. In some embodiments, an acid catalyst may be used, for example, to catalyze the dehydration. The cyclopentanone dehydration can generally take place at conditions sufficient to form water and the cyclopentene product. For example, the cyclopentanone conversion may occur at a temperature of about 25° C. to about 500° C. In some embodiments, the cyclopentanone conversion may be at a about 15 psig (103 kPa) to about 1000 psig (6890 kPa).

When the cyclopentanone compound is contacted by the catalyst, the cyclopentanone compound may be converted to a cyclopentadiene product. In some embodiments, the cyclopentadiene product may include cyclopentene, substituted cyclopentene, and combinations thereof. Examples of suitable cyclopentene products may be represented by Structure 5 and Structure 6, as shown above.

In at least one embodiment, conversion to the five-membered, unsaturated carbocyclic ring may include dehydration of a cyclopentanediol compound (e.g., cyclopentane-1,3-diol) cyclopentadiene product. The dehydration reaction may be conducted in the liquid phase or gas phase. In some embodiments, an acid catalyst may be used, for example, to catalyze the dehydration. In another embodiment, a bifunctional catalyst can be used. The cyclopentanediol dehydration can generally take place at conditions sufficient to form water and the cyclopentadiene product. For example, the cyclopentanediol conversion may occur at a temperature of about 25° C. to about 600° C. In some embodiments, the cyclopentanediol conversion may be at a pressure of about 15 psig (103 kPa) to about 1000 psig (6890 kPa). Hydrogen can be optionally used in the dehydration process, and the hydrogen to cyclopentanediol mole ratio is in the range of 0.1 to 5. Examples of the resulting cyclopentadiene products are shown in Structure 9 and Structure 10.

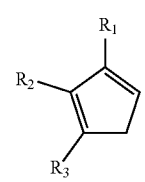

Structure 9

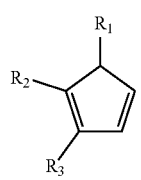

Structure 10

Where R1, R2, and R3 may be individually selected from hydrogen or a hydrocarbyl group containing 1 carbon atom to 10 atoms, wherein the hydrocarbyl group may be linear, branched, or cyclic, and wherein the cyclic hydrocarbyl may aromatic or non-aromatic. The hydrocarbyl group may be substituted or unsubstituted. Alternatively, two or more of R1, R2, and R3 may be connected as part of a ring with 4 carbon atoms to 14 carbons atoms, for example. The ring may be saturated or have multiple degrees of unsaturation, for example, without being aromatic.

In the embodiment where the five-membered carbocyclic ring comprises cyclopentanediol, an acid or a bifunctional catalyst can be used. Suitable acid catalysts may include zeolites, acidic clays, acidic resins, solid phosphoric acid, and acidic metal oxides or a combination thereof. Suitable bifunctional catalyst may include, but are not limited to supported metals on acidic catalysts, including, but are not limited to, metal oxides such as chromium oxide, zinc oxide, vanadium oxide, gallium oxide, rhenium oxide, osmium oxide, ruthenium oxide, iridium oxide, hydrotalcites, metals such as Ni, Co, Fe, Cu, Zn, Pt, Pd, Rh, Ru, Ir, Au, supported metals, clays, aluminosilicates, layered double hydroxides, and amorphous materials.

An embodiment may include conversion of furfural to cyclopentene and/or to cyclopentadiene. For example, furfural may be represented by Structure 1 above with R1, R2, and R3 having hydrogen substitution. Embodiments of the furfural conversion may be represented as illustrated the following reaction:

Reaction 1

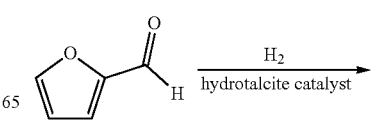

-continued

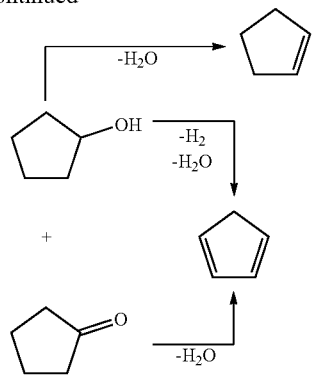

In Reaction 1, the reactions may proceed according to the methods described above. For example, the furfural may be converted to a reaction product by the catalyzed reaction of the furfural with hydrogen, wherein the reaction product comprises cyclopentanol, cyclopentanone, or a combination thereof. While Reaction 1 shows a catalyst supported on hydrotalcite, embodiments may use other suitable supports. Examples of suitable supports may include, but are not limited to, refractory oxides such as titania and/or zirconia; silica; activated carbon; carbon on which is deposited one or more metals selected from titanium, zirconium, vanadium, molybdenum, manganese, and cerium; magnesium oxides; hydrotalcites; other various types of clays; metal-organic frameworks (MOF) and combinations thereof, such as a mixture of two or more of titania, zirconia, and silica. As illustrated, the cyclopentanol and/or cyclopentanone may be dehydrated to produce cyclopentene and/or cyclopentadiene. For example, the cyclopentanol can be dehydrated to produce cyclopentene or dehydrogenated/dehydrated to produce cyclopentadiene. By way of further example, the cyclopentanol may be dehydrated to cyclopentene, which can then be dehydrogenated to cyclopentene. By way of further example, the cyclopentanone may be dehydrated to produce cyclopentadiene.

Exemplary calculated thermodynamic energies of the cyclopentanol to cyclopentene dehydration are provided in the following table, where enthalpy change (ΔH), entropy change (ΔS), change in Gibbs free energy (ΔG), equilibrium constant (K) and logarithm of K (log(K)) are provided. These data demonstrate that dehydration always has a K>1, indicated the product formation is favorable.

TABLE 1

| T (° C.) | ΔH (kcal) | ΔS (cal/K) | ΔG kcal | K | Log(K) |
|---|---|---|---|---|---|
| 0 | 8.194 | 31.583 | −0.433 | 2.22E+00 | 0.347 |
| 50 | 8.296 | 31.927 | −2.021 | 2.33E+01 | 1.367 |
| 100 | 8.399 | 32.225 | −3.625 | 1.33E+02 | 2.124 |
| 150 | 8.489 | 32.45 | −5.243 | 5.10E+02 | 2.708 |
| 200 | 8.552 | 32.591 | −6.869 | 1.49E+03 | 3.173 |
| 250 | 8.583 | 32.655 | −8.5 | 3.56E+03 | 3.551 |
| 300 | 8.582 | 32.654 | −10.133 | 7.32E+03 | 3.864 |
| 350 | 8.551 | 32.602 | −11.765 | 1.34E+04 | 4.127 |
| 400 | 8.493 | 32.512 | −13.393 | 2.23E+04 | 4.349 |
| 450 | 8.412 | 32.397 | −15.016 | 3.46E+04 | 4.538 |
| 500 | 8.314 | 32.267 | −16.632 | 5.04E+04 | 4.702 |
| 550 | 8.205 | 32.13 | −18.242 | 6.98E+04 | 4.844 |
| 600 | 8.09 | 31.994 | −19.845 | 9.28E+04 | 4.968 |
| 650 | 7.977 | 31.868 | −21.442 | 1.19E+05 | 5.077 |
| 700 | 7.87 | 31.755 | −23.032 | 1.49E+05 | 5.173 |
| 750 | 7.778 | 31.663 | −24.618 | 1.82E+05 | 5.259 |

TABLE 1-continued

| T (° C.) | ΔH (kcal) | ΔS (cal/K) | ΔG kcal | K | Log(K) |
|---|---|---|---|---|---|
| 800 | 7.707 | 31.595 | −26.199 | 2.17E+05 | 5.336 |
| 850 | 7.664 | 31.555 | −27.778 | 2.55E+05 | 5.406 |
| 900 | 7.655 | 31.548 | −29.355 | 2.95E+05 | 5.469 |
| 950 | 7.688 | 31.575 | −30.933 | 3.37E+05 | 5.528 |
| 1000 | 7.769 | 31.64 | −32.513 | 3.82E+05 | 5.582 |

Exemplary calculated thermodynamic energies of the cyclopentanone to cyclopentadiene dehydration are provided in the following table, where enthalpy change (ΔH), entropy change (ΔS), change in Gibbs free energy (ΔG), equilibrium constant (K) and logarithm of K (log(K)) are provided. These data demonstrate that dehydration is favorable at temperatures above 300° C.

TABLE 2

| T (° C.) | ΔH (kcal) | ΔS (cal/K) | ΔG kcal | K | Log(K) |
|---|---|---|---|---|---|
| 0 | 20.368 | 35.389 | 10.702 | 2.73E−09 | −8.563 |
| 50 | 20.533 | 35.943 | 8.918 | 9.29E−07 | −6.032 |
| 100 | 20.692 | 36.402 | 7.109 | 6.85E−05 | −4.164 |
| 150 | 20.828 | 36.744 | 5.28 | 1.87E−03 | −2.727 |
| 200 | 20.928 | 36.968 | 3.437 | 2.59E−02 | −1.588 |
| 250 | 20.989 | 37.091 | 1.585 | 2.18E−01 | −0.662 |
| 300 | 21.012 | 37.133 | −0.271 | 1.27E+00 | 0.103 |
| 350 | 21.001 | 37.116 | −2.128 | 5.58E+00 | 0.746 |
| 400 | 20.962 | 37.056 | −3.982 | 1.96E+01 | 1.293 |
| 450 | 20.902 | 36.97 | −5.833 | 5.79E+01 | 1.763 |
| 500 | 20.822 | 36.863 | −7.679 | 1.48E+02 | 2.171 |
| 550 | 20.727 | 36.744 | −9.519 | 3.37E+02 | 2.528 |
| 600 | 20.619 | 36.617 | −11.353 | 6.95E+02 | 2.842 |
| 650 | 20.502 | 36.487 | −13.18 | 1.32E+03 | 3.121 |
| 700 | 20.378 | 36.356 | −15.002 | 2.34E+03 | 3.369 |
| 750 | 20.248 | 36.225 | −16.816 | 3.91E+03 | 3.592 |
| 800 | 20.112 | 36.095 | −18.624 | 6.21E+03 | 3.793 |
| 850 | 19.971 | 35.967 | −20.426 | 9.44E+03 | 3.975 |
| 900 | 19.825 | 35.84 | −22.221 | 1.38E+04 | 4.14 |
| 950 | 19.675 | 35.715 | −24.01 | 1.95E+04 | 4.29 |
| 1000 | 19.519 | 35.59 | −25.792 | 2.68E+04 | 4.428 |

Exemplary calculated thermodynamic energies of the cyclopentanol to cyclopentadiene dehydration and dehydrogenation are provided in the following table, where enthalpy change (ΔH), entropy change (ΔS), change in Gibbs free energy (ΔG), equilibrium constant (K) and logarithm of K (log(K)) are provided. These data demonstrate that dehydration/dehydrogenation of cyclopentanol is also favorable at temperatures above 300° C.

| T (° C.) | ΔH (kcal) | ΔS (cal/K) | ΔG kcal | K | Log(K) |
|---|---|---|---|---|---|
| 0 | 32.164 | 58.627 | 16.15 | 1.19E−13 | −12.923 |
| 50 | 32.541 | 59.892 | 13.186 | 1.21E−09 | −8.919 |
| 100 | 32.901 | 60.93 | 10.165 | 1.11E−06 | −5.954 |
| 150 | 33.226 | 61.749 | 7.097 | 2.16E−04 | −3.666 |
| 200 | 33.504 | 62.37 | 3.993 | 1.43E−02 | −1.845 |
| 250 | 33.728 | 62.822 | 0.863 | 4.36E−01 | −0.361 |
| 300 | 33.9 | 63.137 | −2.287 | 7.45E+00 | 0.872 |
| 350 | 34.022 | 63.342 | −5.449 | 8.15E+01 | 1.911 |
| 400 | 34.098 | 63.459 | −8.619 | 6.29E+02 | 2.799 |
| 450 | 34.133 | 63.51 | −11.794 | 3.67E+03 | 3.565 |
| 500 | 34.134 | 63.511 | −14.969 | 1.71E+04 | 4.232 |
| 550 | 34.106 | 63.476 | −18.144 | 6.57E+04 | 4.818 |
| 600 | 34.058 | 63.42 | −21.317 | 2.17E+05 | 5.336 |
| 650 | 33.996 | 63.35 | −24.486 | 6.27E+05 | 5.797 |
| 700 | 33.928 | 63.278 | −27.652 | 1.62E+06 | 6.211 |
| 750 | 33.861 | 63.212 | −30.814 | 3.82E+06 | 6.583 |

-continued

| T (° C.) | ΔH (kcal) | ΔS (cal/K) | ΔG kcal | K | Log(K) |
|---|---|---|---|---|---|
| 800 | 33.803 | 63.156 | −33.973 | 8.30E+06 | 6.919 |
| 850 | 33.763 | 63.119 | −37.13 | 1.68E+07 | 7.226 |
| 900 | 33.747 | 63.106 | −40.285 | 3.20E+07 | 7.506 |
| 950 | 33.764 | 63.12 | −43.441 | 5.79E+07 | 7.763 |
| 1000 | 33.822 | 63.166 | −46.598 | 9.99E+07 | 8 |

Embodiments may include conversion of a furfural compound to a five-membered, unsaturated carbocyclic ring in a single step. For example, a bifunctional catalyst could be used for the conversion that can both hydrogenate/dehydrogenate and dehydrate, to form the five-membered, unsaturated carbocyclic ring from the furfural compound. The furfural conversion may be conducted in the liquid phase or gas phase. In some embodiments, the furfural conversion may be catalyzed. In some embodiments, a bifunctional catalyst may be used for conversation to the five-membered, unsaturated carbocyclic ring in a single step. Suitable bifunctional catalyst may include, but are not limited to supported metals on acidic catalysts, including, but are not limited to, metal oxides such as chromium oxide, zinc oxide, vanadium oxide, gallium oxide, rhenium oxide, osmium oxide, ruthenium oxide, iridium oxide, hydrotalcites, metals such as Ni, Co, Fe, Cu, Zn, Pt, Pd, Rh, Ru, Ir, Au, supported metals, clays, aluminosilicates, layered double hydroxides, and amorphous materials.

The single-step furfural conversion can generally take place at conditions sufficient to form five-membered, unsaturated carbocyclic ring. For example, the furfural conversion may occur at a temperature of about 20° C. to about 300° C. In some embodiments, the furfural conversion may be at a pressure of about 15 psig (103 kPa) to about 1000 psig (6890 kPa).

When the furfural compound is contacted by the bi-functional catalyst, the furfural compound may be converted to a five-membered, unsaturated carbocyclic ring. In some embodiments, the five-membered, unsaturated carbocyclic ring may include a cyclopentene product, a cyclopentadiene product, and combinations thereof. Examples of suitable cyclopentene products may be represented by Structure 4, as shown above. Examples of suitable cyclopentadiene products may be represented by Structure 5, as shown above.

An embodiment may include conversion of furfural to cyclopentene and/or cyclopentadiene using a bi-functional catalyst. For example, furfural may be represented by Structure 1 above with R1, R2, and R3 having hydrogen substitution. Embodiments of the furfural conversion may be represented as illustrated the following reaction:

Reaction 2

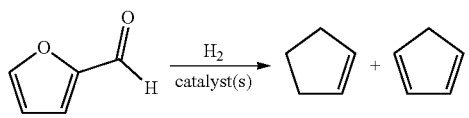

In Reaction 2, the reaction may proceed according to the methods described above. For example, the furfural may be converted to a reaction product by the catalyzed reaction of the furfural with hydrogen, wherein the reaction product comprises cyclopentene, cyclopentadiene, or combinations thereof.

Another embodiment for converting furfural to an intermediate that can be converted to cyclopentadiene includes conversion of furfural to cyclopentanediol that can then be converted to cyclopentene and/or cyclopentadiene. As illustrated in Reaction 4 below, embodiments may include conversion of furfural to furfuryl alcohol by hydrogenation with the furfuryl alcohol then hydrogenated to generate cyclopentanone, shown as 4-hydroxycyclopenet-2en-1-one. In this example, the cyclopentanone may then be converted in the presence of hydrogen and over a hydrogenation catalyst to cyclopentanediol, shown as cyclopentane-1,3-diol:

Reaction 3

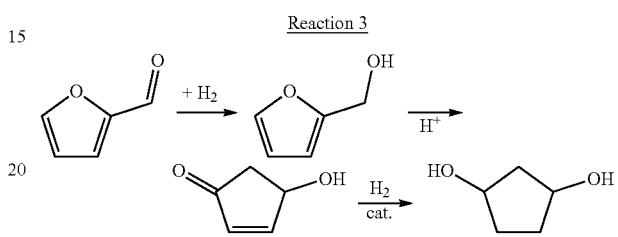

The conversion of furfural to cyclopentanediol, shown as cyclopentane-1,3-diol, may be carried out under any suitable conditions. For example, the furfural conversion may occur at a temperature of about 20° C. to about 300° C. In some embodiments, the furfural conversion may be at a pressure of about 15 psig (103 kPa) to about 1000 psig (6890 kPa). In some embodiments, conversion rates to the cyclopentanediol may be about 90% or greater, about 95% or greater, or about 98% or greater. These conversion rates are on a molar basis. Suitable catalysts may include, but are not limited to, metal oxides such as chromium oxide, zinc oxide, vanadium oxide, gallium oxide, rhenium oxide, osmium oxide, ruthenium oxide, iridium oxide, hydrotalcites, metals such as Ni, Co, Fe, Cu, Zn, Pt, Pd, Rh, Ru, Ir, Au, supported metals, clays, aluminosilicates, layered double hydroxides, and amorphous materials. In some embodiments, the catalyst may be a supported catalyst that includes a catalyst deposited on a support. Examples of suitable supports may include, but are not limited to, refractory oxides such as titania and/or zirconia; activated carbon; carbon on which is deposited one or more metals selected from titanium, zirconium, vanadium, molybdenum, manganese, and cerium; magnesium oxides; hydrotalcites; other various types of clays; metal-organic frameworks (MOF) and combinations thereof, such as a mixture of two or more of titanic, zirconia, and silica. Exemplary catalysts are Pt/C, Pd—Cu/C, and Ni based catalysts such as Ni—Cu or Cu—Co supported on refractory oxides shown above or zeolites (e.g., Faujasite) or mesoporous materials (e.g., MCM-41, SBA-15), Ru supported on refractory oxides shown above or zeolites (e.g., Faujasite) or mesoporous materials (e.g., MCM-41, SBA-15), CuZnAl oxides, and CuNiAl. A specific example of a bifunctional catalyst may include a metal functionality of Sn—Pt and an acid component of a zeolite. Another specific example of a bifunctional catalyst may include a metal functionality of Pt and an acid component of a zeolite.

The cyclopentanediol may then be converted under certain conditions and in the presence of a catalyst to cyclopentene and/or cyclopentadiene. By way of example, conversion of cyclopentane-1,3diol to cyclopentadiene is shown Reaction 4 below.

Reaction 4

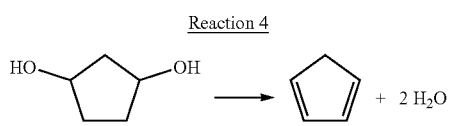 [SMILES: OC1CCC(O)C1 ; C1=CCC=C1]

In some embodiments, the cyclopentanediol conversion may occur at a temperature of about 100° C. to about 400° C. In some embodiments, the cyclopentanediol may be at a pressure of about 5 psig (34.5 kPa) to about 1000 psig (6890 kPa). In some embodiments, suitable catalysts may include bifunctional catalysts that contain hydrogenation dehydrogenation metal functionality and a heterogenous acid component. Examples of suitable hydrogenation dehydrogenation metal functionality may include, but are not limited to, Sn, Pd, Pt, Ni, Rh, Ru, Ni, Co, and combinations thereof. Examples of suitable acid components may include a heterogeneous acid component, for example, zeolite, mixed metal oxides, and resins, which may have an alpha test value of less than 100 and, in some embodiments, less than 50. In some embodiments, the loading of metal on the acidic component may be in the range of about 0.1 wt % to about 5 wt % (referenced to the catalyst weight), or about 0.3 wt % to about 3 wt %, or about 0.5 wt % to about 2 wt %. When the acidic component is an inorganic acid, in some embodiments, the acidic component can be self-bonded or bonded using a binder such as silica, alumina, titania, zirconia, clay (e.g., Kaolin), or combinations thereof. Examples of the acidic component include zeolites having the structure of MFI, MWW, BEA, MOR, or FAU. Optionally, the zeolite component can be further stabilized using phosphorus, rare earths such as lanthanum, yttrium. When the acidic component is mixed metal oxides, in some embodiments, examples of mixed metal oxides may include zirconium tungsten oxides, zirconium molybdenum oxides, sulfated zirconia, or mixtures thereof. A specific example of bifunctional catalyst may include a metal functionality of Sn—Pt and an acid component of a zeolite, for example, Pt—Sn/ZSM-5 or Pt—Sn/MCM-49. Another example of a specific catalyst may include a metal functionality of Pt and an acid component of a zeolite such as Pt/MCM-49. Any suitable reaction configuration may be used for the cyclopentanediol conversion, including, but not limited to, a batch reactor, a semi-batch reactor, a fixed bed reactor, a slurry reactor, or a fluidized-bed reactor.

In addition to the previously described cyclopentadiene, cyclopentanediol may be converted to a number of products based on factors, such as catalyst selection and reaction conditions. By way of example, cyclopentainediol may converted to cyclopentene-ol by co-feeding hydrogen, as shown in Reaction 5 below. As further shown in Reaction 5, the cyclopentene-ol may be converted to cyclopentenone, which may then be converted to further products such as heavy oxygenated and coke.

Accordingly, the preceding description describes examples of processes and systems for producing five-membered carbocyclic rings that are unsaturated, such as cyclopentadiene and cyclopentadiene. The processes and systems disclosed herein may include any of the various features disclosed herein, including one or more of the following embodiments.

Embodiment 1. A method for conversion of furfural compounds, comprising:

converting a furfural compound to at least a five-membered, saturated carbocyclic ring; and converting the five-membered, saturated carbocyclic ring in a presence of a catalyst to at least a five-membered, unsaturated carbocyclic ring, wherein the five-membered, unsaturated carbocyclic ring is selected from the group consisting of a cyclopentene product, a cyclopentadiene product, and combinations thereof.

Embodiment 2. The method of embodiment 1, where the catalyst comprises a bifunctional catalyst comprising a hydrogenation/dehydrogenation metal functionality and a heterogenous acid component.

Embodiment 3. The method of embodiment 1 or 2, wherein the converting the furfural compound and the converting the five-membered, saturated carbocyclic ring occur in a single step over a bi-functional catalyst using at least one reactor selected from the group consisting of a fixed bed reactor, a batch reactor, a slurry reactor, a semi-batch reactor, and a fluidized-bed reactor.

Embodiment 4. The method of any one of embodiments 1 to 3, wherein the furfural compound is represented by Structure 1, wherein the cyclopentene product is represented by at least one of Structure 5 or Structure 6, and wherein the cyclopentadiene product is represented at least one of Structure 7 or Structure 8.

Embodiment 5. The method of any one of embodiments 1 to 4, wherein the converting the furfural compound is at a temperature of about 20° C. to about 400° C.' and about 15 psig to about 1000 psig, and wherein the five-membered, saturated carbocyclic ring is selected from the group consisting of cyclopentanol, cyclopentanone, cyclopentanediol, and combinations thereof.

Embodiment 6. The method of any one of embodiments 1 to 5, wherein the converting the five-membered, saturated carbocyclic ring comprises dehydrating the five-membered, saturated carbocyclic ring comprising a cyclopentanol product to product at least water and the cyclopentene product.

Embodiment 7. The method of embodiment 6, further comprising dehydrogenating the cyclopentene product to produce at least hydrogen and the cyclopentadiene product, wherein the dehydrating is at a temperature of about 25° C. to about 300° C. and about 15 psig to about 1000 psig.

Embodiment 8. The method of any one of embodiments 1 to 5, wherein the converting the five-membered, saturated carbocyclic ring comprises dehydrating the five-membered, saturated carbocyclic ring comprising a cyclopentanone product to produce at least water and the cyclopentadiene product, wherein the dehydrating is at a temperature of about 25° C. to about 500° C. and about 15 psig to about 1000 psig.

Embodiment 9. The method of any one of embodiments 1 to 8, wherein the furfural compound comprises furfural, and wherein the five-membered, unsaturated carbocyclic ring comprises a combination of cyclopentene and cyclopentadiene, and wherein the five-membered, saturated carbocyclic ring comprises a combination of cyclopentanol and cyclopentanone.

Embodiment 10. The method of any one of embodiments 1 to 5, wherein the furfural compound is catalytically converted to cyclopentane-1,3-diol, and wherein the cyclopentane-1,3-diol is converted to the cyclopentadiene.

Embodiment 11. The method of embodiment 10, wherein the catalyst comprises a bifunctional catalyst.

Embodiment 12. The method of embodiment 11, wherein the bifunctional catalyst comprises a hydrogenation/dehydrogenation metal functionality and a heterogenous acid component, wherein the hydrogenation/dehydrogenation metal functionality comprises at least metal selected from the group consisting of Pd, Pt, Ni, Rh, Ru, Ni, Co, and combinations thereof, and wherein the heterogeneous acid component comprises at least component selected from the group consisting of a zeolite, a mixed metal oxide, a resins, and combinations thereof, where the acidic component has an alpha value of less than 100.

Embodiment 13. The method of any one of embodiments 1 to 12, wherein products of the converting the furfural compound comprising the five-membered, saturated carbocyclic ring are not purified prior to the step of converting the five-membered, saturated carbocyclic ring.

Embodiment 14. A method for conversion of furfural compounds, comprising: contacting furfural and hydrogen with a catalyst to produce at least a five-membered, saturated carbocyclic ring, wherein the five-membered, saturated carbocyclic ring is selected from the group consisting of cyclopentanol, cyclopentanone, cyclopentanediol, and combinations thereof; and contacting the five-membered, saturated carbocyclic ring with a catalyst to produce at least water and a five-membered, unsaturated carbocyclic ring, wherein the five-membered, unsaturated carbocyclic ring is selected from the group consisting of cyclopentene, cyclopentadiene, and combinations thereof.

Embodiment 15. The method of embodiment 14, wherein the contacting the five-membered, saturated carbocyclic ring comprises dehydrating the five-membered, saturated carbocyclic ring comprising the cyclopentanol to produce the five-membered, unsaturated carbocyclic ring comprising the cyclopentene.

Embodiment 16. The method of embodiment 14, wherein the contacting the five-membered, saturated carbocyclic ring comprises dehydrating and dehydrogenating the five-membered, saturated carbocyclic ring comprising the cyclopentanol to produce the five-membered, unsaturated carbocyclic ring comprising the cyclopentadiene.

Embodiment 17. The method of embodiment 14, wherein the contacting the five-membered, saturated carbocyclic ring comprises dehydrating the five-membered, saturated carbocyclic ring comprising the cyclopentanone to produce the five-membered, unsaturated carbocyclic ring comprising the cyclopentadiene.

Embodiment 18. The method of embodiment 14, wherein the furfural is catalytically converted to cyclopentane-1,3-diol, and wherein the cyclopentane-1,3-diol is converted to cyclopentadiene.

Embodiment 20. A method for conversion of furfural compounds, comprising: hydrogenating furfural by catalytically reacting the furfural and hydrogen to produce a five-membered, saturated carbocyclic ring, wherein the five-membered, saturated carbocyclic ring is selected from the group consisting of cyclopentanol, cyclopentanone, cyclopentanediol and combinations thereof; and converting the five-membered, saturated carbocyclic ring to cyclopentadiene.

Embodiment 20. The method of embodiment 19, wherein the hydrogenating furfural and the converting the five-membered, saturated carbocyclic ring occur in a single step over a bi-functional catalyst.

EXAMPLES

To facilitate a better understanding of the present disclosure, the following examples of certain aspects of some embodiments are given. In no way should the following examples be read to limit, or define, the entire scope of the disclosure.

Example 1

A ZSM-5 catalyst for use in furfural conversion was prepared as follows:
1. An aqueous zeolite slurry was prepared using 9.46 grams of zeolite.
2. To this slurry, 9.54 grams of $P_2O_5$ was added via phosphoric acid addition. Sufficient water was added to form a spray dryer feed slurry upon addition of the clay.
3. To this slurry, 81 grams of kaolin clay were added.
4. The slurry was then spray dried to the desired particle size distribution to form powder.
5. The powder was calcined in air in a rotary calciner with an average bed temperature of about 540° C.
6. The powder was then steamed in a rotary calciner having an average shell temperature between about 900° C. to about 1070° C. and sufficient residence time to impart the desired catalyst performance.
7. Preparation of 1% Pt+0.3% Sn/ZSM-5

The sample was prepared by sequential impregnations. $SnCl_2$ was added to ZSM-5 by impregnation of aqueous solutions of tin chloride. The Sn metal oxide loading on ZSM-5 as Sn was 0.3 wt %. After impregnating, the sample was dried in air at 120° C. for 4 hrs. Pt was added to ZSM-5 containing Sn by impregnating with aqueous solutions of $(NH_3)_4Pt(NO_3)_2$. The Pt metal loading on the supports was 1 wt %. After impregnating, the sample was dried in air at (120° C. for 4 hours), and then calcined at 360° C. in air for 3 hours.

Besides tin chloride ($SnCl_2$), tin (II) tartrate hydrate was also used as Sn precursor compound for deposition of Sn on alumina support.

A series of samples containing different Pt and Sn loadings on ZSM-5 spray drier were also prepared similarly. The Pt and Sn contents of the different samples were 1% Pt+0.30% Sn/ZSM-5, 1.5% Pt+0.30% Sn/ZSM-5, and 2.0% Pt+0.50% Sn/ZSM-5.

The calcination effect of the Sn precursor compound before Pt deposition was also studied. After impregnation of tin chloride, and/or tin tartrate, onto a ZSM-5 containing Sn was dried in air at 120° C. for 4 hours and, and then calcined at 538° C. in air for 3 hours. Afterwards, Pt was added to ZSM-5 containing Sn by impregnation of aqueous solution of $(NH_3)_4Pt(NO_3)_2$. The sample containing Sn and Pt was dried in air at 120° C. for 4 hours, and then calcined at 360° C. in air for 3 hours. The sample was activated under 100 CC/min $H_2$ flow and at 350 psig (2413 kpa) and 280° C.

Example 2

Another example catalyst for furfural conversion was synthesized. The catalyst comprised 0.6 wt % Pt/MCM-49 (80 wt % MCM-49/20 wt % Alumina, 1/20" Q). For catalyst synthesis, 80 parts MCM-49 zeolite crystals were combined with 20 parts pseudoboehmite alumina, on a calcined dry weight basis. The MCM-49 and pseudoboehmite alumina dry powder were then placed in a muller or a mixer and mixed for about 10 to about 30 minutes. Sufficient water and 0.05% polyvinyl alcohol were added to the MCM-49 and alumina during the mixing process to produce an extrudable paste. The extrudable paste was formed into a 1/20 inch quadralobe extrudate using an extruder. After extrusion, the 1/20th inch quadralobe extrudate was dried at a temperature ranging from 250° F. (121° C.) to 325° F. (168° C.). After drying, the dried extrudate was heated to 1000° F. (538° C.)

under flowing nitrogen. The extrudate was then cooled to ambient temperature and humidified with saturated air or steam.

After the humidification, the extrudate was ion exchanged with 0.5 to 1 N ammonium nitrate solution. The ammonium nitrate solution ion exchange was repeated. The ammonium nitrate exchanged extrudate was then washed with deionized water to remove residual nitrate prior to calcination in air. After washing the wet extrudate, it was dried. The exchanged and dried extrudate was then calcined in a nitrogen/air mixture to a temperature 1000° F. (538° C.).

Pt was added to MCM-49 by impregnating with aqueous solutions of $(NH_3)_4Pt(NO_3)_2$. The Pt metal loading on the supports was 0.6 wt %. After impregnating, the sample was dried in air at (120° C. for 4 hours), and then calcined at 360° C. in air for 3 hours. The sample was then activated under 100 CC/min $H_2$ flow and at 350 psig (2413 kpa) and 280° C.

Example 3

This example was performed to evaluate reactor loading the catalyst from Examples 1 and 2. The reactor used in these experiments comprised of a stainless steel tube. The Standard Reactor: ⅜ in (9.5 mm)×20.5 in (52 cm)×0.035 in (0.89) wall thickness. A piece of stainless steel tubing 8¾ in. (22.2 cm) long×⅜ in. (9.5 mm) o.d and a piece of ¼ in (6.4 mm) tubing of similar length was used in the bottom of the reactor as a spacer (one inside of the other) to position and support the catalyst in the isothermal zone of the furnace. A ¼ in (6.4 mm) plug of glass wool was placed at the top of the spacer to keep the catalyst in place. A ⅛ in (3.2 mm) stainless steel thermo-well was placed in the catalyst bed, long enough to monitor temperature throughout the catalyst bed using a movable thermocouple.

The catalyst was loaded with a spacer at the bottom to keep the catalyst bed in the center of the furnace's isothermal zone. Typically 4.0 g of cat is sized to 14-25 mesh (710 micro meter). When loaded the catalyst bed measures about 12.5 cm in height. The reactor was topped off with the same size quartz or larger size up to 14 mesh.

The catalyst was then loaded into the reactor from the top. The catalyst bed typically was 10 cm. in length. A ¼ ¼ in (6.4 mm) of glass wool was placed at the top of the catalyst bed to separate quartz chips from the catalyst. The remaining void space at the top of the reactor was filled with quartz chips. The reactor was installed in the furnace with the catalyst bed in the middle of the furnace at the pre-marked isothermal zone. The reactor was then pressure and leak tested typically at 800 psig (5516 kpa).

500 cc ISCO syringe pumps were used to introduce the feed to the reactor and MFC is used to introduce the hydrogen to the reactor at certain ratios. The feed was cyclopentane-1,3diol. Since cyclopentane-1,3diol is a solid at room temperature, 10% water was added to cyclopentane-1,3diol and the blend (feed A) was fed to the reactor using ISCO pumps. A MITY MITE back pressure controller was used to control the reactor pressure typically at 1000 psig. On-line gas chromatography analyses were taken to verify feed and the product composition. The cyclopentadiene products exiting the reactor flowed through heated lines routed to gas chromatography then to collection pots. The non-condensable gas products routed through a gas pump for analyzing the gas effluent. Material balances were for 24-hour intervals. Samples were taken for analysis. The material balance and the gas samples were taken at the same time while an on-line gas chromatography analysis was conducted for doing material balance The two catalysts from Examples 1 and 2 were evaluated at different temperature and different feed composition. Table 3 below summarizes the reaction conditions and results.

TABLE 3

| Catalyst | Feed | Water/cyclopentane-1,3diol mol ratio | Hydrogen/cyclopentane-1,3diol mol ratio | Temp ° C. | Conv. Wt % | Selectivity |
| --- | --- | --- | --- | --- | --- | --- |
| None | A | None | None | 450 | 38 | <1% |
| Example 1 | A | 1:1 | 2:1 | 450 | 60 | 46 |
| Example 2 | A | 1:1 | 2:1 | 450 | 78 | 26 |

While the disclosure has been described with respect to a number of embodiments and examples, those skilled in the art, having benefit of this disclosure, will appreciate that other embodiments can be devised which do not depart from the scope and spirit of the disclosure as disclosed herein. Although individual embodiments are discussed, the present disclosure covers all combinations of all those embodiments.

While compositions, methods, and processes are described herein in terms of "comprising," "containing," "having," or "including" various components or steps, the compositions and methods can also "consist essentially of" or "consist of" the various components and steps. The phrases, unless otherwise specified, "consists essentially of" and "consisting essentially of" do not exclude the presence of other steps, elements, or materials, whether or not, specifically mentioned in this specification, so long as such steps, elements, or materials, do not affect the basic and novel characteristics of the disclosure, additionally, they do not exclude impurities and variances normally associated with the elements and materials used.

All numerical values within the detailed description and the claims herein modified by "about" or "approximately" with respect the indicated value are intended to take into account experimental error and variations that would be expected by a person having ordinary skill in the art.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited.

The invention claimed is:

1. A method for conversion of furfural compounds, comprising:
    converting a furfural compound to at least a five-membered, saturated carbocyclic rings wherein the five-membered, saturated carbocyclic ring is selected from the group consisting of a cyclopentanol product, a cyclopentanone product, a cyclopentanediol product, and combinations thereof; and converting the five-membered, saturated carbocyclic ring to at least a five-membered, unsaturated carbocyclic ring, wherein the five-membered, unsaturated carbocyclic ring is selected from the group consisting of a cyclopentene product, a cyclopentadiene product, and combinations thereof;

wherein the cyclopentanol product comprises cyclopentanol, a substituted cyclopentanol, or a combination thereof;

wherein the cyclopentanone product comprises cyclopentanone, a substituted cyclopentanone, or a combination thereof;

wherein the cyclopentanediol product comprises cyclopentanediol, a substituted cyclopentanediol, or a combination thereof;

wherein the cyclopentene product comprises cyclopentene, a substituted cyclopentene, or a combination thereof;

wherein the cyclopentadiene product comprises cyclopentadiene, a substituted cyclopentadiene, or a combination thereof; and wherein the converting the furfural compound and the converting the five-membered, saturated carbocyclic ring occur in a single step over a bifunctional catalyst comprising a hydrogenation/dehydrogenation metal and a heterogenous acid component.

2. The method of claim 1, wherein the converting the furfural compound and the converting the five-membered, saturated carbocyclic ring occur in at least one reactor selected from the group consisting of a fixed bed reactor, a batch reactor, a slurry reactor, a semi-batch reactor, and a fluidized-bed reactor.

3. The method of claim 1, wherein the furfural compound is represented by the following structure:

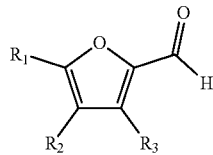

wherein R1, R2, and R3 are individually selected from hydrogen or a hydrocarbyl group containing 1 carbon atom to 10 carbon atoms, and wherein the hydrocarbyl group is linear, branched, an aromatic cyclic hydrocarbyl, or a non-aromatic cyclic hydrocarbyl;

wherein the cyclopentene product is represented by at least one of the following structures:

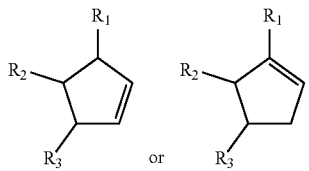

wherein the cyclopentadiene product is represented at least one of the following structures:

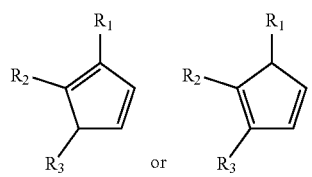

wherein R1, R2, and R3 are individually selected from hydrogen or a hydrocarbyl group containing 1 carbon atom to 10 carbon atoms, and wherein the hydrocarbyl group is linear, branched, an aromatic cyclic hydrocarbyl, or a non-aromatic cyclic hydrocarbyl.

4. The method of claim 1, wherein the converting the furfural compound is at a temperature of about 20° C. to about 400° C. and at a pressure of about 15 psig to about 1000 psig, and wherein the five-membered, saturated carbocyclic ring is selected from the group consisting of cyclopentanol, cyclopentanone, cyclopentanediol, and combinations thereof.

5. The method of claim 1, wherein the converting the five-membered, saturated carbocyclic ring comprises dehydrating the five-membered, saturated carbocyclic ring comprising the cyclopentanol product to produce at least water and the cyclopentene product.

6. The method of claim 5, further comprising dehydrogenating the cyclopentene product to produce at least hydrogen and the cyclopentadiene product, wherein the dehydrating is at a temperature of about 25° C. to about 300° C. and at a pressure of about 15 psig to about 1000 psig.

7. The method of claim 1, wherein the converting the five-membered, saturated carbocyclic ring comprises dehydrating the five-membered, saturated carbocyclic ring comprising the cyclopentanone product to produce at least water and the cyclopentadiene product, wherein the dehydrating is at a temperature of about 25° C. to about 500° C. and at a pressure of about 15 psig to about 1000 psig.

8. The method of claim 1, wherein the furfural compound comprises furfural, and wherein the five-membered, unsaturated carbocyclic ring comprises a combination of cyclopentene and cyclopentadiene, and wherein the five-membered, saturated carbocyclic ring comprises a combination of cyclopentanol and cyclopentanone.

9. The method of claim 1, wherein the five-membered, saturated carbocyclic ring comprises cyclopentane-1,3-diol, and wherein the cyclopentane-1,3-diol is converted to the cyclopentadiene.

10. The method of claim 9, wherein the hydrogenation/dehydrogenation metal comprises at least one metal selected from the group consisting of Pd, Pt, Ni, Rh, Ru, Ni, Co, and combinations thereof, and wherein the heterogenous acid component comprises at least one component selected from the group consisting of a zeolite, a mixed metal oxide, a resin, and combinations thereof, where the heterogenous acid component has an alpha value of less than 100.

11. The method of claim 1, wherein products of the converting the furfural compound comprising the five-membered, saturated carbocyclic ring are not purified prior to the step of converting the five-membered, saturated carbocyclic ring.

12. A method for conversion of furfural compounds, comprising:
- contacting furfural and hydrogen with a catalyst to produce at least a five-membered, saturated carbocyclic ring, wherein the five-membered, saturated carbocyclic ring is selected from the group consisting of cyclopentanol, cyclopentanone, cyclopentanediol, and combinations thereof; and
- contacting the five-membered, saturated carbocyclic ring with a catalyst to produce at least water and a five-membered, unsaturated carbocyclic ring, wherein the five-membered, unsaturated carbocyclic ring comprises.

13. The method of claim 12, wherein the contacting the five-membered, saturated carbocyclic ring comprises dehydrating and dehydrogenating the five-membered, saturated carbocyclic ring comprising the cyclopentanol to produce the five-membered, unsaturated carbocyclic ring comprising the cyclopentadiene.

14. The method of claim 12, wherein the contacting the five-membered, saturated carbocyclic ring comprises dehydrating the five-membered, saturated carbocyclic ring comprising the cyclopentanone to produce the five-membered, unsaturated carbocyclic ring comprising the cyclopentadiene.

15. The method of claim 12, wherein the five-membered, saturated carbocyclic ring comprises cyclopentane-1,3-diol, and wherein the cyclopentane-1,3-diol is converted to cyclopentadiene.

16. A method for conversion of furfural compounds, comprising:
- hydrogenating furfural by catalytically reacting the furfural and hydrogen to produce a five-membered, saturated carbocyclic ring, wherein the five-membered, saturated carbocyclic ring is selected from the group consisting of cyclopentanol, cyclopentanone, cyclopentanediol and combinations thereof; and
- converting the five-membered, saturated carbocyclic ring to cyclopentadiene;
- wherein the hydrogenating furfural and the converting the five-membered, saturated carbocyclic ring occur in a single step over a bifunctional catalyst comprising a hydrogenation/dehydrogenation metal and a heterogenous acid component.

* * * * *